(12) United States Patent
Ishida (10) Patent No.: US 11,471,174 B2
(45) Date of Patent: Oct. 18, 2022

(54) STENT SYSTEM

(71) Applicant: Biomedical Solutions Inc., Tokyo (JP)

(72) Inventor: Hiroki Ishida, Tokyo (JP)

(73) Assignee: BIOMEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 17/019,034

(22) Filed: Sep. 11, 2020

(65) Prior Publication Data

US 2021/0077132 A1    Mar. 18, 2021

(30) Foreign Application Priority Data

Sep. 18, 2019    (JP) .............................. JP2019-169164

(51) Int. Cl.
*A61B 17/22*    (2006.01)

(52) U.S. Cl.
CPC .... *A61B 17/22* (2013.01); *A61B 2017/22045* (2013.01); *A61B 2017/22072* (2013.01)

(58) Field of Classification Search
CPC . A61B 17/22; A61B 17/221; A61B 17/22031; A61B 17/12022; A61B 17/2215; A61B 17/320725; A61B 17/1204; A61B 2017/22045; A61B 2017/22072; A61B 2017/22034; A61B 2017/22094; A61B 2017/22035; A61B 2090/034; A61F 2/07; A61F 2/02; A61F 2/06; A61F 2/82; A61F 2/2418; A61F 2/2436; A61F 2/86; A61F 2/88; A61F 2/89; A61F 2/90; A61F 2/966; A61F 2002/823; A61F 2002/828; A61F 2002/826
See application file for complete search history.

(56) References Cited

U.S. PATENT DOCUMENTS

| | | | | |
|---|---|---|---|---|
| 7,837,702 | B2 * | 11/2010 | Bates | A61F 2/014 606/200 |
| 9,820,761 | B2 * | 11/2017 | Garrison | A61M 25/0108 |
| 2009/0192518 | A1 * | 7/2009 | Golden | A61F 2/966 606/108 |
| 2009/0198269 | A1 * | 8/2009 | Hannes | A61B 17/221 606/200 |
| 2011/0054504 | A1 | 3/2011 | Porter | |

(Continued)

FOREIGN PATENT DOCUMENTS

| | | |
|---|---|---|
| DE | 102011100733 A1 | 11/2012 |
| JP | 2014525796 A | 10/2014 |

(Continued)

OTHER PUBLICATIONS

Extended European Search Report issued in EP Application 26196009.3, dated Feb. 18, 2021, 6 pages.

*Primary Examiner* — Jocelin C Tanner
(74) *Attorney, Agent, or Firm* — Muncy, Geissler, Olds & Lowe, P.C.

(57) ABSTRACT

A stent system according to the present invention is for use in retrieving a blood clot from the brain region and includes a wire; a first stent connected to a distal portion of the wire; a first outer sheath that covers and is fixed to a portion of the wire proximal to the first stent; and a second stent disposed on a portion of the wire proximal to the first stent, in which the second stent is configured to be movable toward or away from the first stent.

9 Claims, 11 Drawing Sheets

(56) References Cited

U.S. PATENT DOCUMENTS

| | | | |
|---|---|---|---|
| 2013/0030461 A1* | 1/2013 | Marks | A61B 17/221 606/200 |
| 2013/0317589 A1* | 11/2013 | Martin | A61B 17/3207 623/1.2 |
| 2015/0112376 A1* | 4/2015 | Molaei | A61B 17/22031 606/200 |
| 2016/0220265 A1* | 8/2016 | Pokorney | A61B 17/221 |
| 2018/0132876 A1 | 5/2018 | Zaidat | |
| 2019/0000492 A1 | 1/2019 | Casey et al. | |

FOREIGN PATENT DOCUMENTS

| | | |
|---|---|---|
| JP | 2019-005587 A | 1/2019 |
| WO | WO-2013/016435 A1 | 1/2013 |
| WO | WO-2019-022145 A1 | 1/2019 |

\* cited by examiner

STENT SYSTEM

This application is based on and claims the benefit of priority from Japanese Patent Application No. 2019-169164, filed on 18 Sep. 2019, the content of which is incorporated herein by reference.

BACKGROUND OF THE INVENTION

Field of the Invention

The present invention relates to a stent system including a wire and a stent connected to a distal portion of the wire.

Related Art

A known example of a stent system for capturing a blood clot formed in a blood vessel includes a wire and a stent connected to a distal portion of the wire (see, for example, Patent Document 1). When such a stent system is used, the stent is used through a catheter to capture a blood clot, which is followed by withdrawing the wire from the body through the catheter so that the stent, which is connected to the wire and captures the blood clot, is withdrawn from the body. As a result, the blood clot is removed.

The stent capturing the blood clot may be thick or the blood clot may become hard, which may make it difficult to insert the overall length of the stent into the microcatheter. Techniques to address such a case include placing the stent capturing the blood clot as near to the microcatheter as possible; and withdrawing the microcatheter together with the stent capturing the blood blot through a guiding catheter while placing, in the microcatheter, a proximal portion of the stent capturing the blood clot.

Patent Document 1: Japanese Unexamined Patent Application, Publication No. 2019-005587

SUMMARY OF THE INVENTION

Unfortunately, even if successfully captured with the stent, the blood clot may come off of the stent during the course of withdrawing the stent from the body. In addition, some blood clots are difficult to securely capture depending on their size or hardness. The problem will be significant if, during the course of withdrawing the stent from the body, the captured blood clot passes through a blood vessel discontinuously increasing in diameter due to confluence of the blood vessels.

It is an object of the present invention to provide a stent system having an improved ability to capture a blood clot in the brain region.

(1) The present invention relates to a stent system for use in retrieving a blood clot from a brain region, the stent system including: a wire; a first stent connected to a distal portion of the wire; a first outer sheath that covers and is fixed to a portion of the wire proximal to the first stent; a second stent disposed on a portion of the wire proximal to the first stent, the second stent being configured to be movable toward or away from the first stent.

(2) The second stent may have an expandable and contractible opening on a side facing the first stent.

(3) The second stent may be configured to be movable toward the first stent so as to be disposed at a position facing at least a proximal portion of the first stent.

(4) The stent system may further include a second outer sheath that covers and is fixed to a portion of the wire proximal to the second stent, wherein the first outer sheath limits the range in which the second stent is movable toward the distal side, and the second outer sheath limits the range in which the second stent is movable toward the proximal side.

(5) The second stent may be configured to be closable so as to abut against both a proximal end of the first outer sheath and a distal end of the second outer sheath.

(6) The present invention also relates to a stent system including: a wire; a first stent connected to a distal portion of the wire; and a second stent disposed on a portion of the wire proximal to the first stent, the stent system being configured such that, when delivered to a brain region, the stent system is movable toward the proximal side while holding a blood clot between the first and second stents after the first stent engages with the blood clot.

(7) The stent system may be for use in a patient who has passed eight hours or more after blood clot formation.

(8) The first stent may be configured to expand while at least a portion of the first stent is located distal to a blood clot.

The present invention makes it possible to provide a stent system having an improved ability to capture a blood clot in the brain region.

DETAILED DESCRIPTION OF THE INVENTION

Figure 1A:
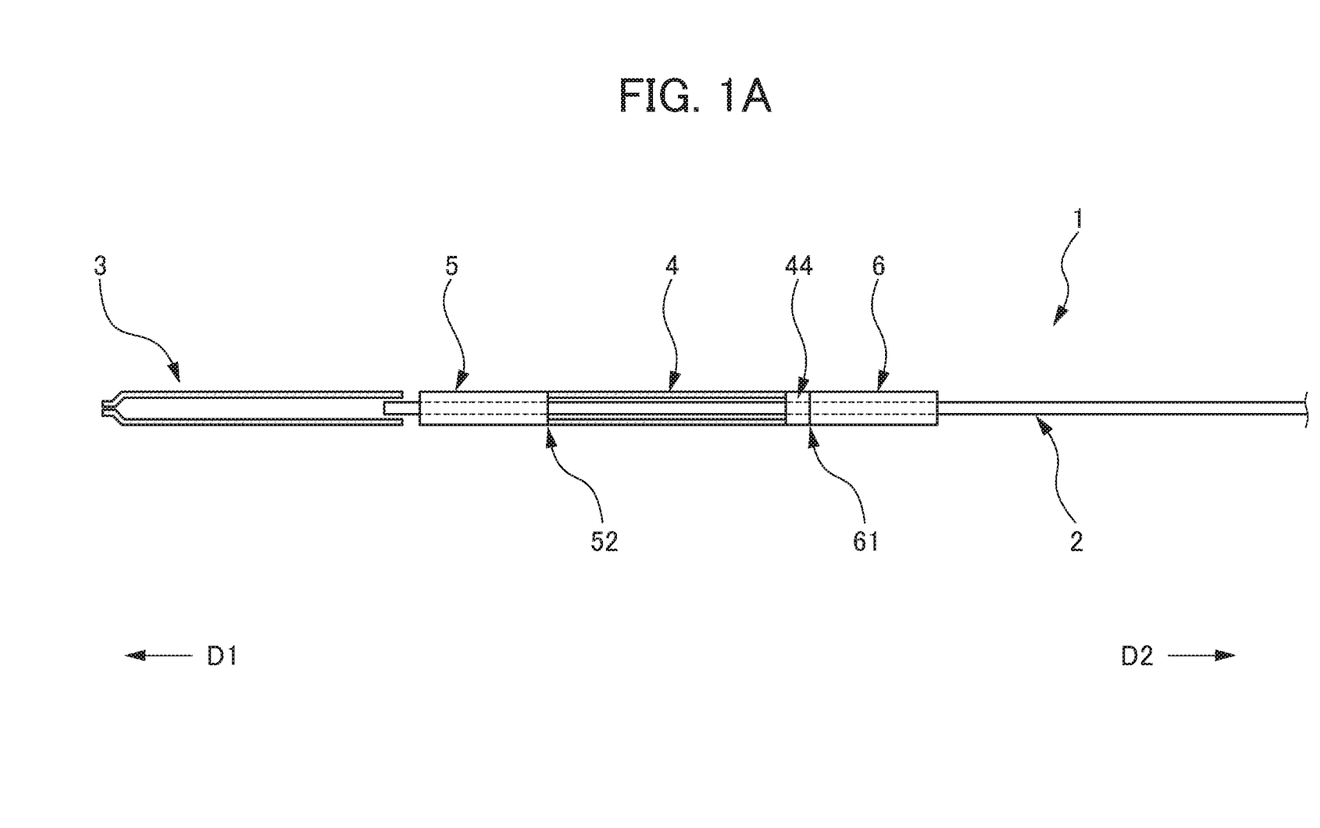
FIG. 1A is a schematic diagram showing a stent system according to an embodiment of the present invention, in which a stent is in a radially closed state, when the stent is inserted in a microcatheter.
Figure 1B:
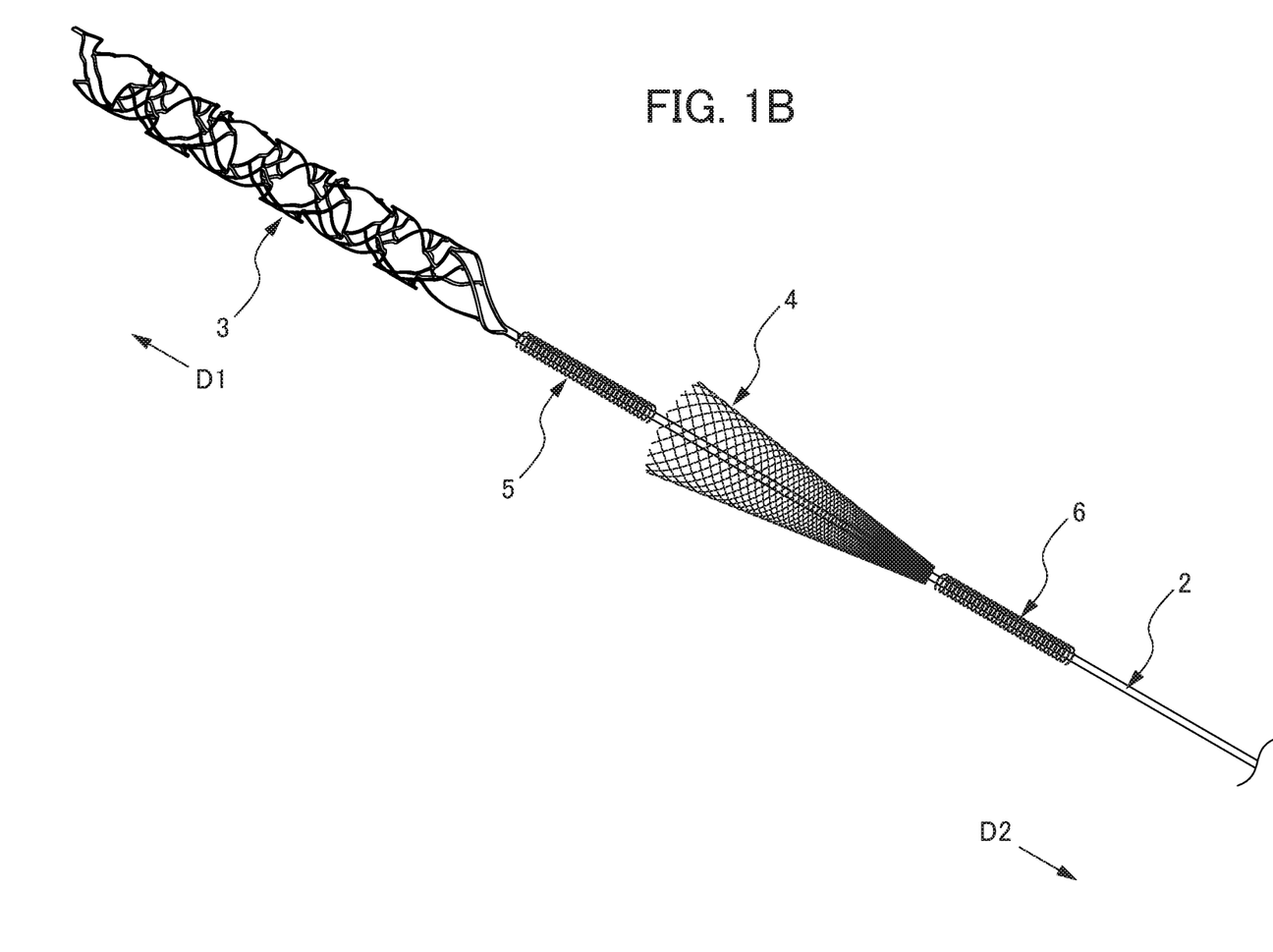
FIG. 1B is a perspective view showing the stent system according to an embodiment of the present invention, in which the stent is in an expanded state, when it is removed from the microcatheter.
Figure 2A:
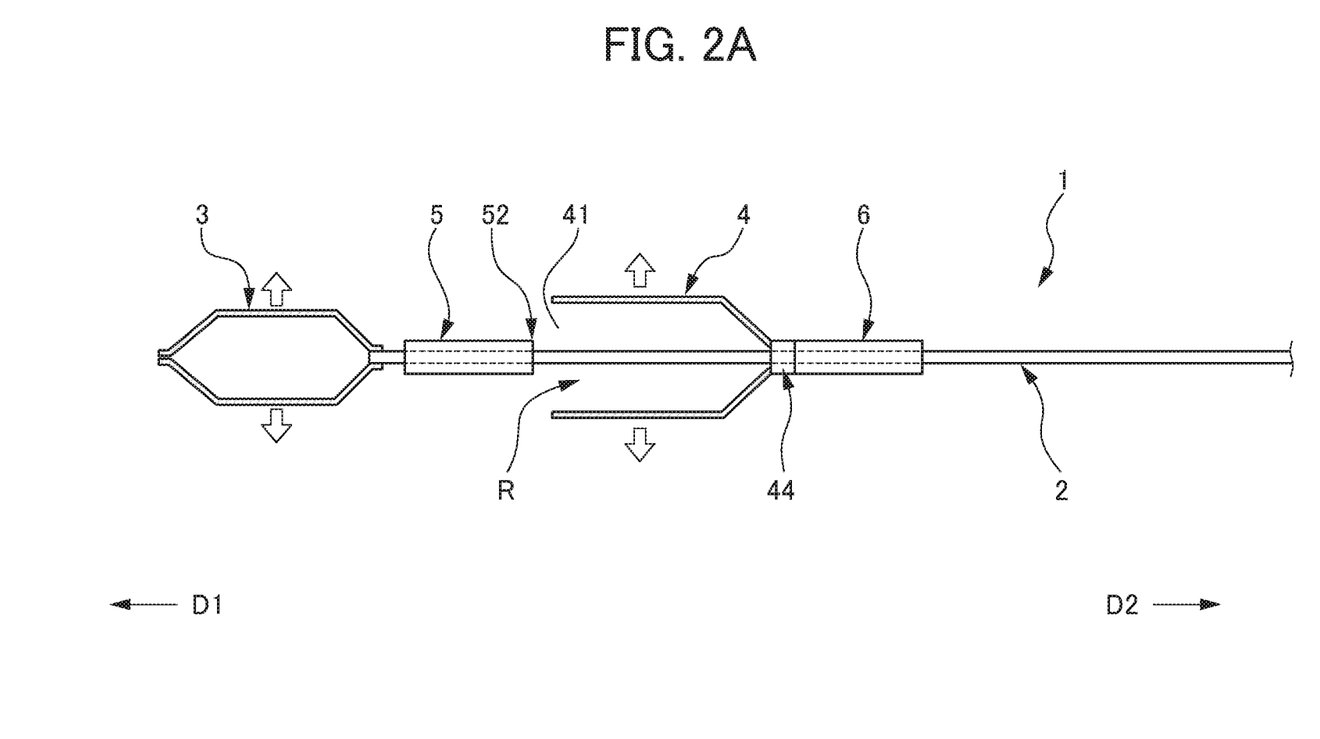
FIG. 2A is a schematic diagram showing the stent system according to an embodiment of the present invention, in which the stent is in the expanded state.
Figure 2B:
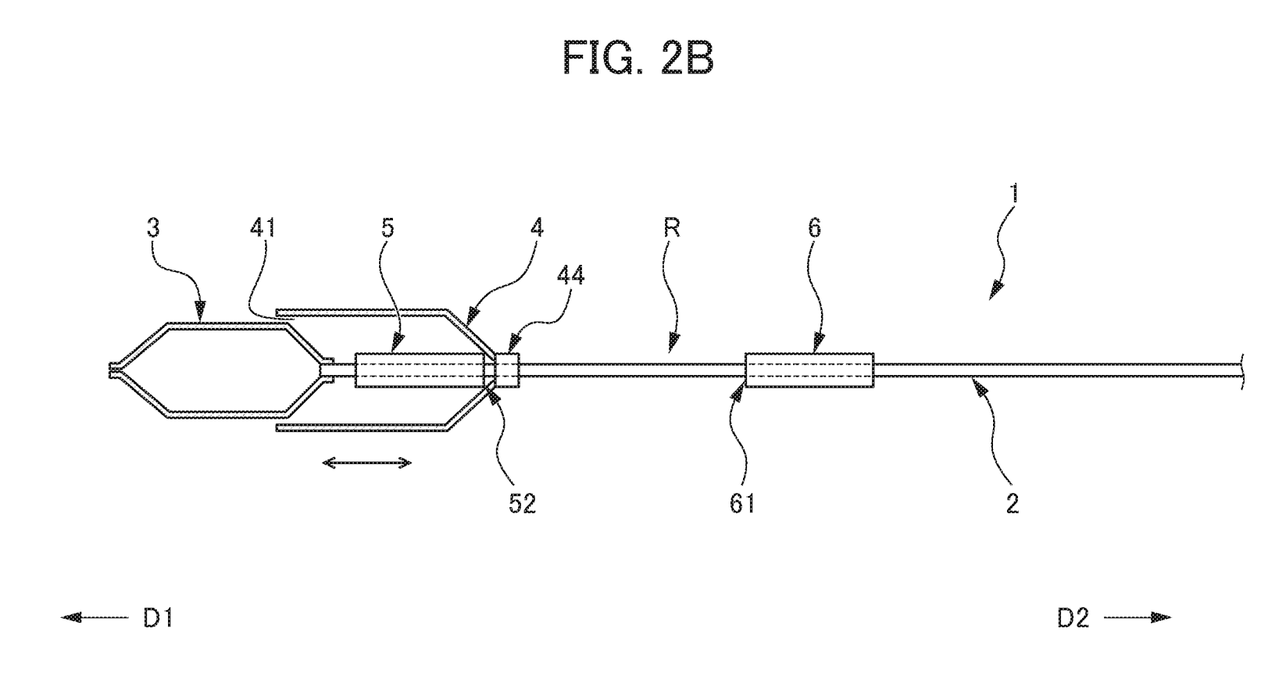
FIG. 2B is a schematic diagram showing a first stent and a second stent moved closer to the first stent from the position shown in FIG. 2A.
Figure 3A:
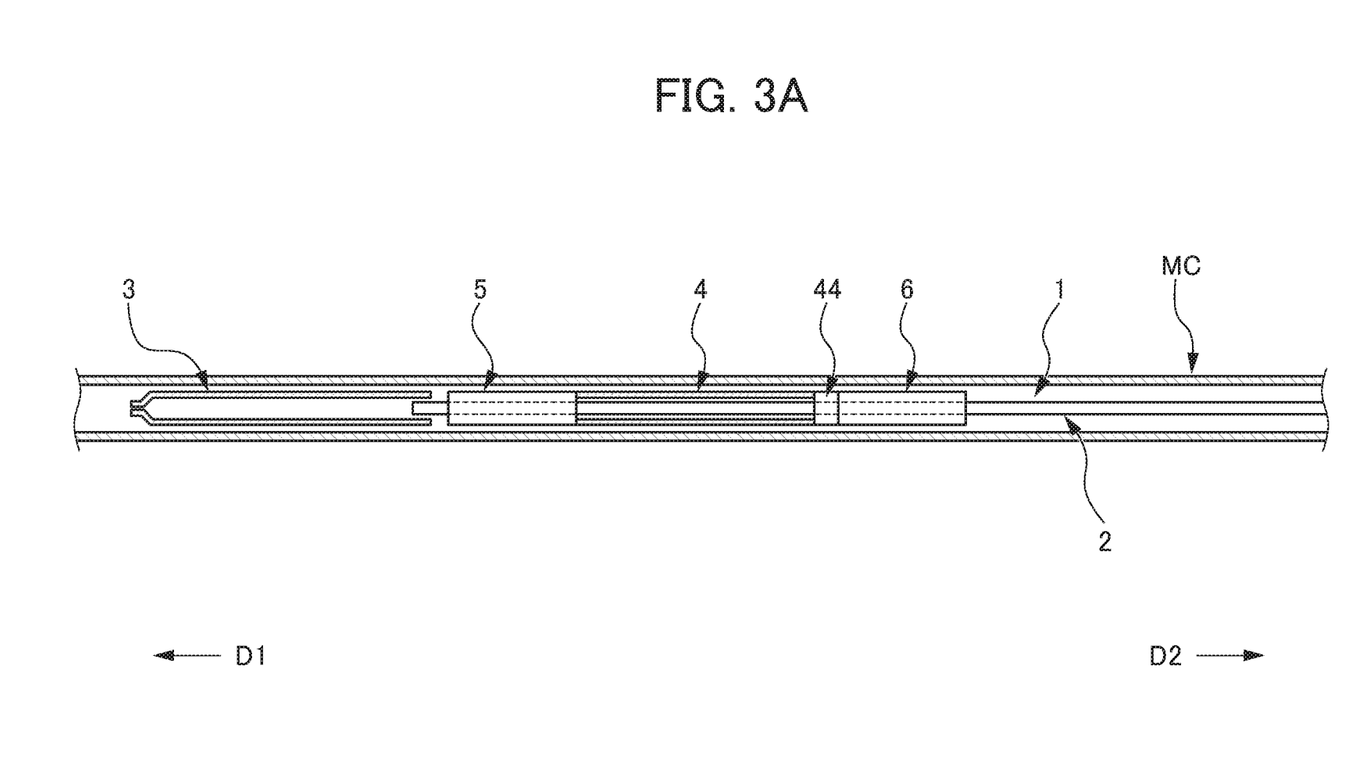
FIG. 3A is a schematic cross-sectional view showing the stent system according to an embodiment inserted in a microcatheter.
Figure 3B:
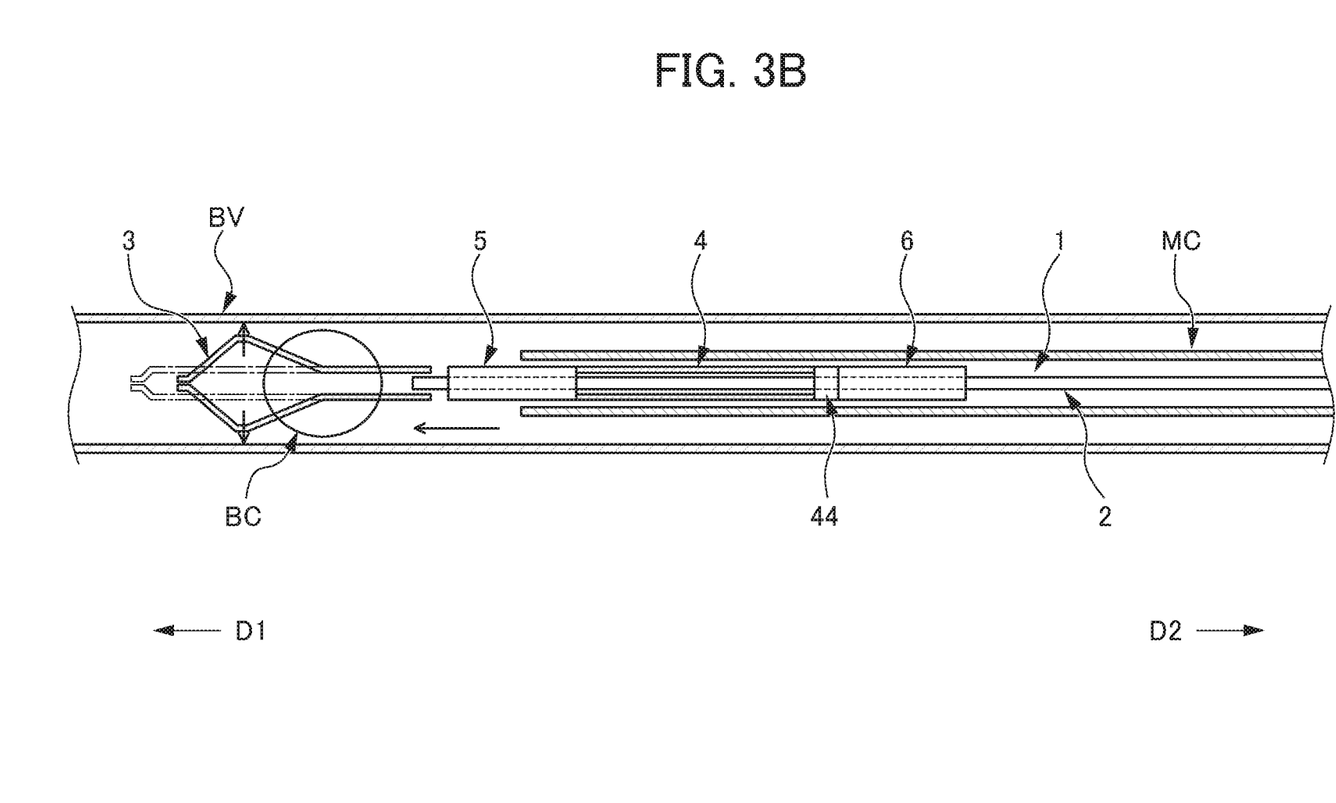
FIG. 3B is a schematic cross-sectional view showing that the first stent engages with a blood clot when moved out of the microcatheter from the position shown in FIG. 3A.
Figure 3C:
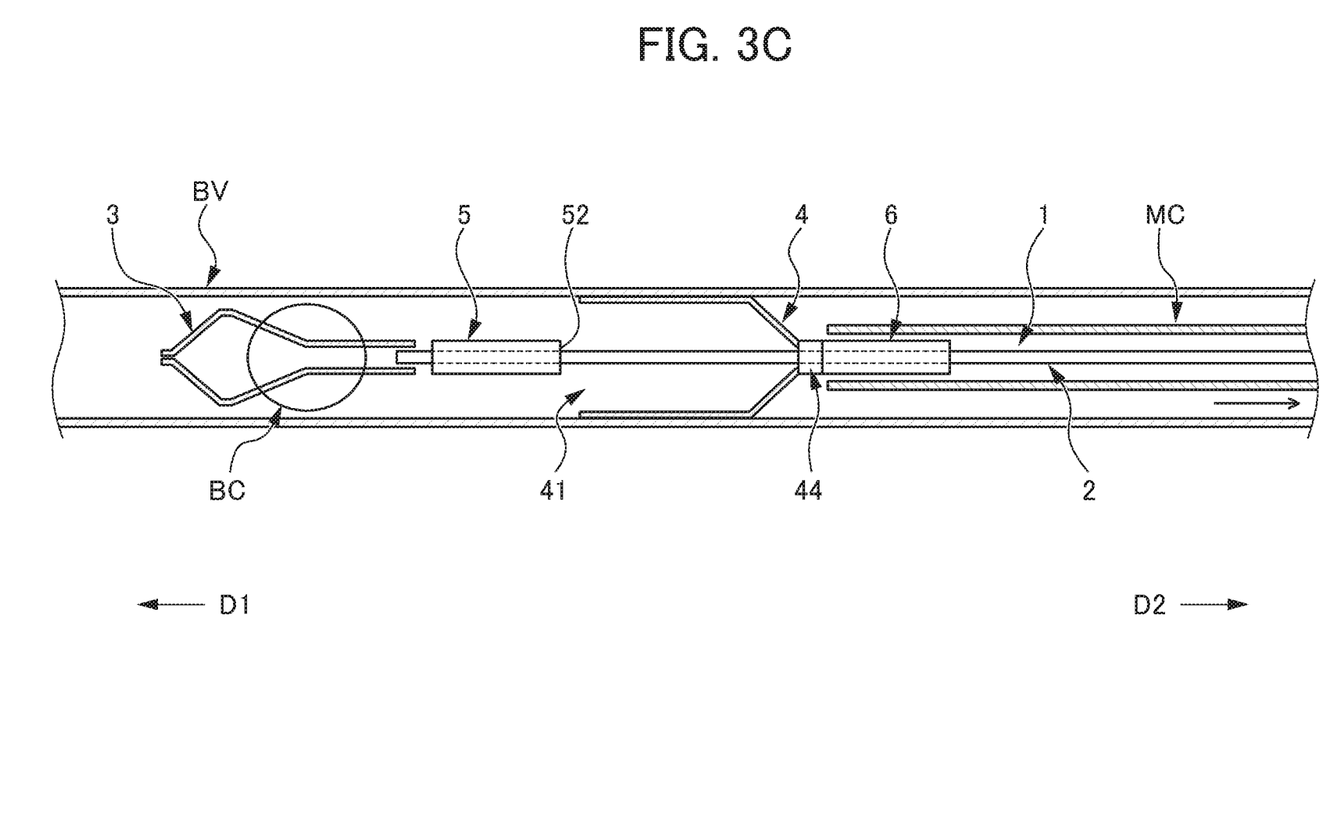
FIG. 3C is a schematic cross-sectional view showing that the second stent is expanded when the second stent is moved out of the microcatheter from the position shown in FIG. 3B.
Figure 3D:
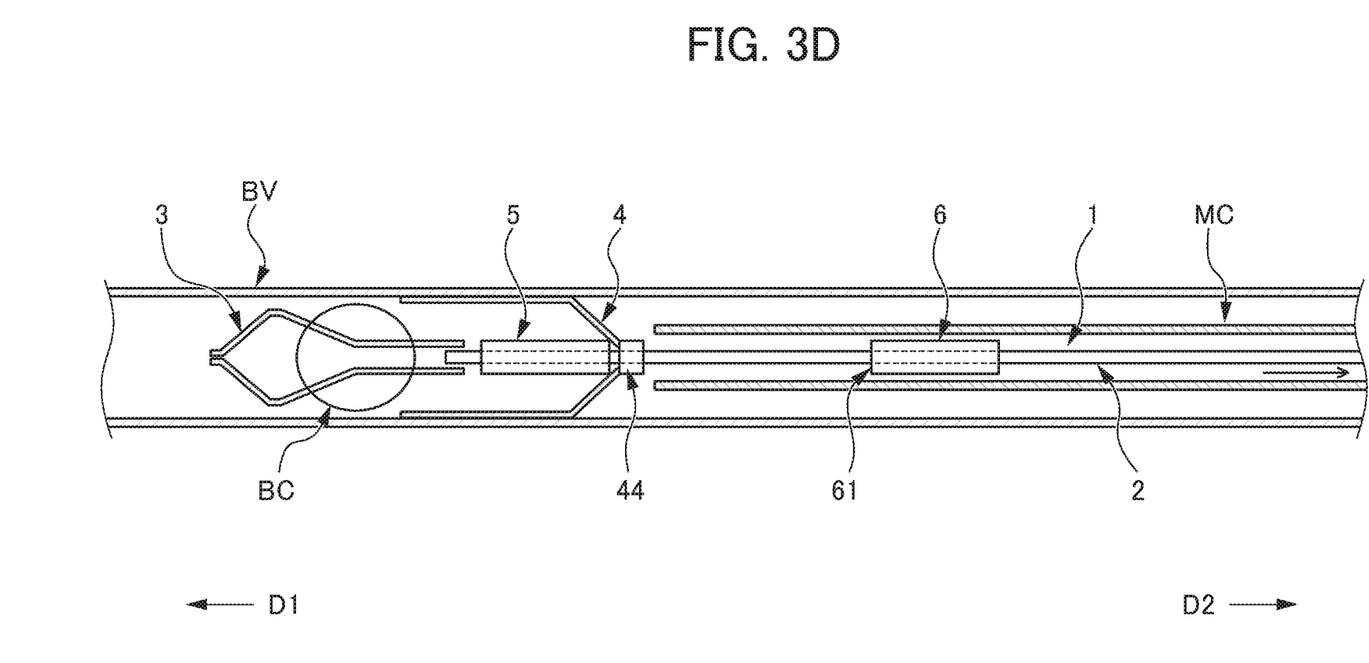
FIG. 3D is a schematic cross-sectional view showing that the first stent, which engages with the blood clot, is moved closer to the second stent from the position shown in FIG. 3C.
Figure 3E:
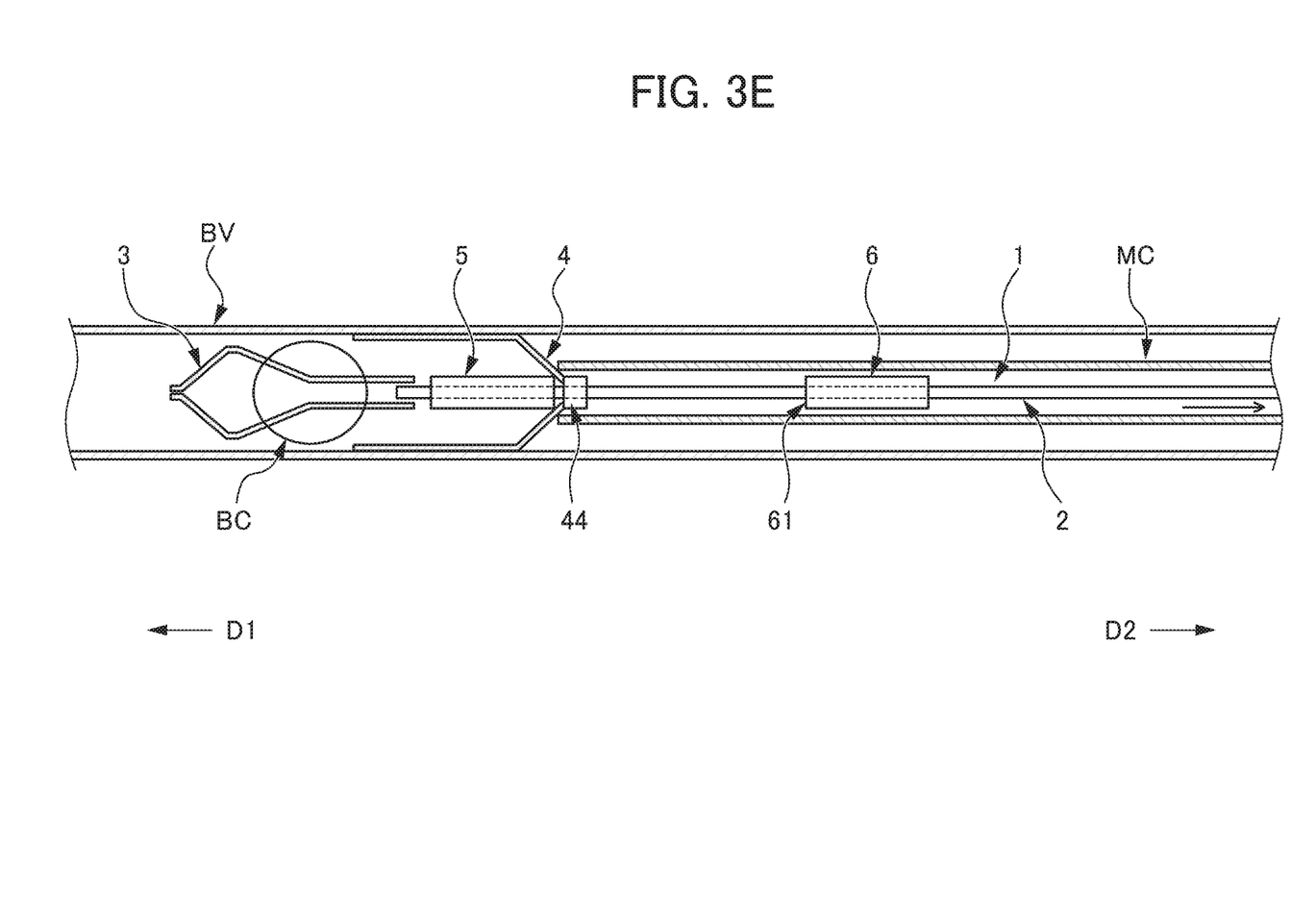
FIG. 3E is a schematic cross-sectional view showing the second stent brought from the position shown in FIG. 3D into contact with the distal opening of the microcatheter.
Figure 3F:
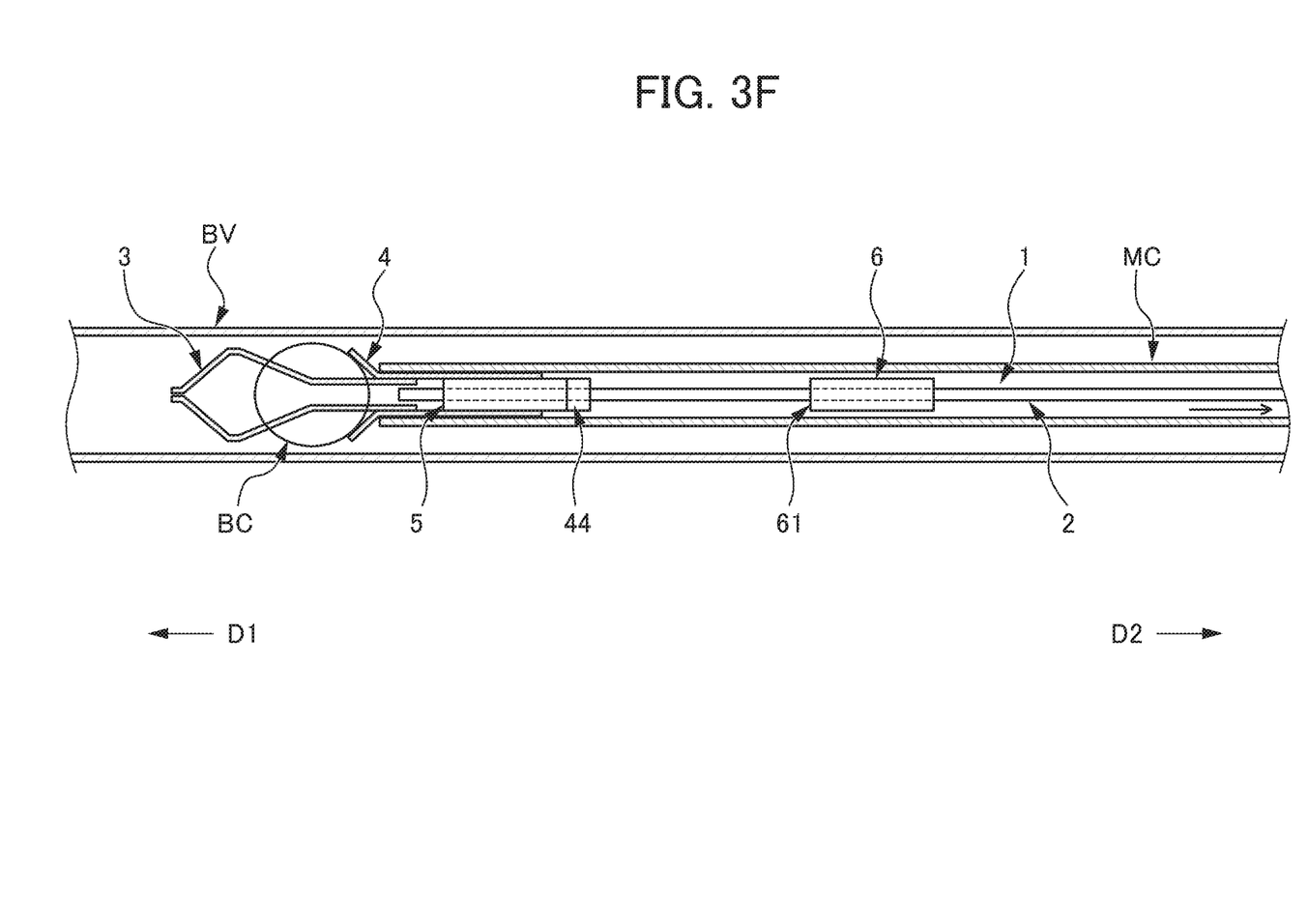
FIG. 3F is a schematic cross-sectional view showing the stent system according to an embodiment of the present invention moved from the position shown in FIG. 3E to the position in which the stent system is housed in the microcatheter.
Figure 3G:
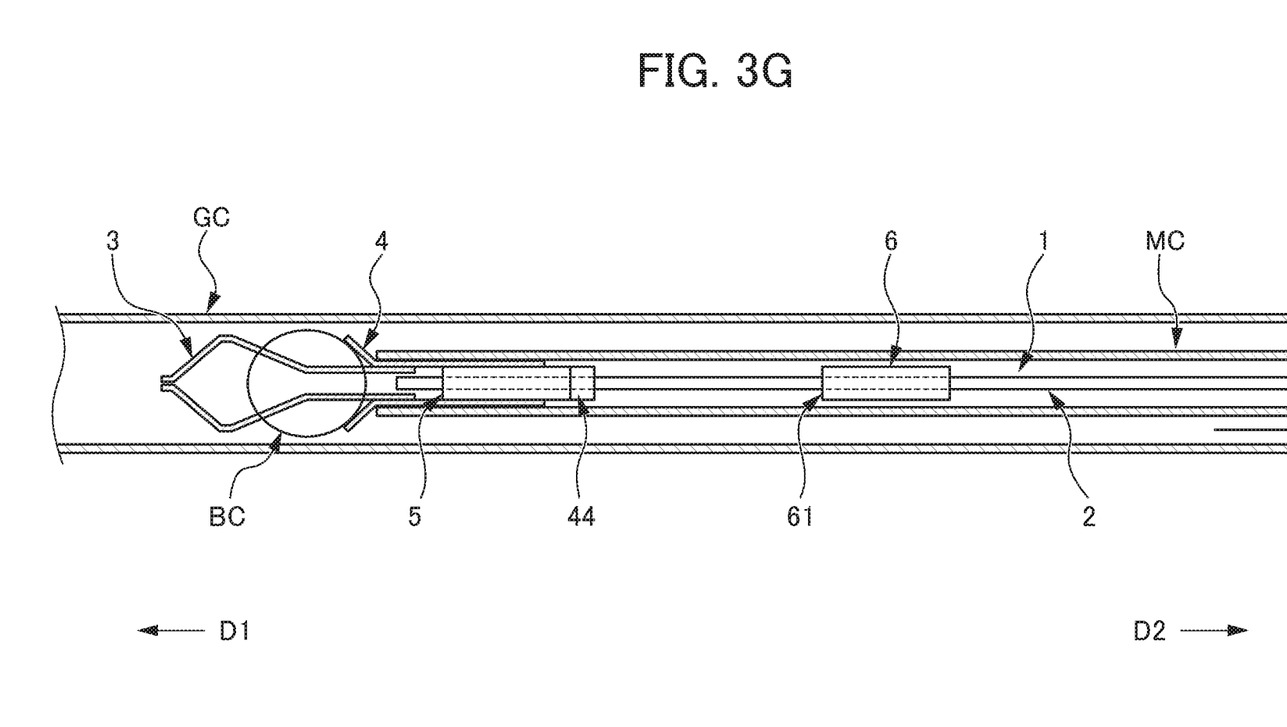
FIG. 3G is a schematic cross-sectional view showing the stent system moved from the position shown in FIG. 3F, in which it is housed in the microcatheter, to the position in which it is inserted in a guiding catheter and moved in the guiding catheter.

Hereinafter, a stent system according to an embodiment of the present invention will be described with reference to the drawings. FIG. 1A is a schematic diagram showing a stent system according to an embodiment of the present invention, in which a stent is in a radially closed state, when the stent is inserted in a microcatheter. FIG. 1B is a perspective view showing the stent system according to an embodiment of the present invention, in which the stent is in an expanded state, when it is removed from the microcatheter. FIG. 2A is a schematic diagram showing the stent system according to an embodiment of the present invention, in which the stent is in the expanded state. FIG. 2B is a schematic diagram showing a first stent and a second stent moved closer to the first stent from the position shown in FIG. 2A. FIG. 3A is a schematic cross-sectional view showing the stent system according to an embodiment of the present invention inserted in a microcatheter. FIG. 3B is a schematic cross-sectional view showing that the first stent engages with a blood clot when moved out of the microcatheter from the position shown in FIG. 3A. FIG. 3C is a schematic cross-sectional view showing that the second stent is expanded when the second stent is moved out of the microcatheter from the position shown in FIG. 3B. FIG. 3D is a schematic cross-sectional view showing that the first stent, which engages with the blood clot, is moved closer to the second stent from the position shown in FIG. 3C. FIG. 3E is a schematic cross-sectional view showing the second stent brought from the position shown in FIG. 3D into contact with the distal opening of the microcatheter. FIG. 3F is a schematic cross-sectional view showing the stent system moved from the position shown in FIG. 3E to the position in which the stent system is housed in the microcatheter. FIG. 3G is a schematic cross-sectional view showing the stent system moved from the position shown in FIG. 3F, in which it is housed in the microcatheter, to the position in which it is inserted in a guiding catheter and moved in the guiding catheter. In the drawings, arrows D1 and D2 indicate the distal side or position and the proximal side or position, respectively.

As shown in FIG. 1A to 2B, a stent system 1 according to an embodiment includes a wire 2, a first stent 3, a first coil 5 as a first outer sheath, a second stent 4, and a second coil 6 as a second outer sheath.

The wire 2 is also called a pusher wire, which is moved toward the distal side D1 to push the first stent 3 to a target site in a biological organ such as a blood vessel, and moved toward the proximal side D2 to withdraw the stent 3 from the body after the first stent 3 engages with a blood clot.

The first stent 3 is connected to a distal portion of the wire 2. In general, the first stent 3 has a mesh structure. Alternatively, the first stent 3 may have any other structure which can engage with a blood clot.

The first coil 5 covers and is fixed to a portion of the wire 2, which is proximal to the first stent 3. Part of the overall length of the first coil 5 may be fixed to the wire 2. The proximal end 52 of the first coil 5 also functions as an abutment face, against which the distal end of the second stent 4 abuts when the second stent 4 is in the radially closed state. The first outer sheath is not limited to a coil and may be any other member that can cover and be fixed to the wire 2, such as a tube.

The second stent 4 is disposed on a portion of the wire 2, which is proximal to the first stent 3. The second stent 4 will be described in detail later.

The second coil 6 covers and is fixed to a portion of the wire 2, which is proximal to the second stent 4. Part of the overall length of the second coil 6 may be fixed to the wire 2. The distal end 61 of the second coil 6 also functions as an abutment face, against which the proximal end of the second stent 4 abuts. The second outer sheath is not limited to a coil and may be any other member that can cover and be fixed to the wire 2, such as a tube. A coil-free region R, in which no coil is disposed, is provided between the proximal end 52 of the first coil 5 and the distal end 61 of the second coil 6.

The second stent 4 is configured to be movable toward or away from the first stent 3. In other words, from the reverse point of view, the first stent 3 is configured to be movable toward or away from the second stent 4. In the present disclosure, the first and second stents 3 and 4 are moved relative to each other.

The second stent 4 includes a marker member 44 at its proximal end. The marker member 44 functions as a marker. The marker member 44 has a through hole penetrating in the longitudinal direction of the wire 2 so that the marker member 44 is movable in the coil-free region R in the longitudinal direction of the wire 2. This makes the whole of the second stent 4 movable in the longitudinal direction of the wire 2. On the other hand, the first coil 5 limits the range in which the second stent 4 is movable toward the distal side D1, and the second coil 6 limits the range in which the second stent 4 is movable toward the proximal side D2.

Specifically, as shown in FIG. 1A, the marker member 44 can move toward the proximal side D2 until its proximal end abuts against the distal end 61 of the second coil 6. As shown in FIG. 2S, the marker member 44 can also move toward the distal side D1 until its distal end abuts against the proximal end 52 of the first coil 5. It should be noted that, depending on the structure of the marker member 44, the main body of the second stent 4 abuts against the proximal end 52 of the first coil 5 before the distal end of the marker member 44 abuts against the proximal end 52 of the first coil 5.

As shown in FIGS. 2A and 2S, the second stent 4 is expandable (radially expandable) in the radial direction (perpendicular to the longitudinal direction of the wire 2). The second stent 4 has an expandable and contractible opening 41 on its distal side facing the first stent 3. As shown in FIG. 2B, when expanded, the opening 41 can be moved beyond the first coil 5 to a position facing at least a proximal portion of the first stent 3. From a different point of view, when moved toward the first stent 3 side (distal side D1), the second stent 4 can be disposed at a position facing at least a proximal portion of the first stent 3.

In addition, the second stent 4 is configured to be closable so as to abut against both the proximal end 52 of the first coil 5 and the distal end 61 of the second coil 6. From a different point of view, in such an abutment state, the second stent 4 is in a radially closed state and fitted in the coil-free region R. In this state, the second stent 4 has an outer diameter substantially equal to the outer diameters of the first and second coils 5 and 6, so that the level of smoothness for the stent system 1 to pass through a microcatheter is substantially the same as that without the second stent 4.

The second stent 4 is more expandable than the first stent 3. The expanded second stent 4 may or may not push the inner surface of a blood vessel BV radially outward, depending on the inner diameter of the blood vessel BV, which includes cases where a balloon is used to expand the blood vessel BV. In the states shown in FIGS. 3C to 3E, which will be described later, the second stent 4 does not push the inner surface of a blood vessel BV radially outward.

Next, an example of a method for using the stent system 1 will be described with reference to FIGS. 3A to 3G. A guiding catheter (not shown) is placed in the body of a patient. A microcatheter MC is inserted into the guiding catheter, and the stent system 1 is inserted into the microcatheter MC (see FIG. 3A). The stent system 1 is in the radially closed state as shown in FIG. 1A. The stent system 1 is delivered to and placed in the brain region (with vascular diameters of at most 6 mm in general).

As shown in FIG. 3B, while the distal opening of the microcatheter MC is placed near a blood clot BC, the wire 2 is pushed toward the distal side D1 to push the first stent 3 from the distal opening of the microcatheter MC. The first stent 3 penetrates the blood clot BC. When at least a portion of the first stent 3 is placed distal to the blood clot BC, the first stent 3 is expanded (radially expanded or deployed) so that the first stent 3 engages with the blood clot BC. In this embodiment, the first stent 3 is not completely expanded since the resistance of the blood clot BC to the expansion force of the first stent 3 is relatively high. More specifically, the portion of the first stent 3 distal to the blood clot BC can be expanded to the maximum since the resistance of the blood clot BC less affects it. On the other hand, portions of the first stent 3 inside and proximal to the blood clot BC are less expandable due to the resistance of the blood clot BC. As a result, a proximal portion of the blood clot BC is exposed outside of the first stent 3.

The microcatheter MC is then withdrawn toward the proximal side D2 while the wire 2 is held. In this way, the second stent 4 in the radially closed state is exposed out of the distal opening of the microcatheter MC. When exposed out of the microcatheter MC, the second stent 4 is expanded (radially expanded or deployed) as shown in FIG. 3C to push the inner surface of the blood vessel BV radially outward. The expanded second stent 4 is not easily movable relative to the blood vessel BV.

The wire 2 is then withdrawn toward the proximal side D2 so that the first stent 3, which has engaged with the blood clot BC, is moved toward the proximal side D2, namely, toward the second stent 4 side while the position of the second stent 4 is maintained. Consequently, as shown in FIG. 3D, the blood clot BC, with which the first stent 3 has engaged, particularly a portion of the blood clot BC exposed outside of the first stent 3, is pressed against or covered by the second stent 4. The second stent 4 may have a structure capable of completely covering the blood clot BC (to prevent the blood clot BC from being exposed outside and to avoid contact between the blood clot BC and the inner surface of the blood vessel BV or the microcatheter MC). If possible, the first stent 3 may be further moved toward the proximal side D2 until the proximal end 52 of the first coil 5 abuts against the second stent 4 so that the first coil 5 can no longer move toward the proximal side D2.

When the wire 2 is withdrawn toward the proximal side D2 while the microcatheter MC is held, the second stent 4 is moved toward the proximal side D2 as a result of being pushed by the first stent 3, the blood clot BC, and the first coil 5. In this way, the second stent 4 abuts against the distal opening of the microcatheter MC (see FIG. 3E). It should be noted that a proximal portion of the second stent 4 may enter the interior of the microcatheter MC through its distal opening.

When the wire 2 is further withdrawn toward the proximal side D2 from this position while the microcatheter MC is held, the expanded stent 4 can be moved toward the proximal side of the microcatheter MC. Consequently, as shown in FIG. 3F, proximal portion of the second stent 4 is placed in the microcatheter MC while the blood clot BC, with which the first stent 3 has engaged, is held between the first and second stents 3 and 4. The first stent 3 and the blood clot BC engaged therewith are not placed in the microcatheter MC since they remain larger than the inner diameter of the microcatheter MC. As shown in FIG. 3G, the stent system 1 with a portion remaining exposed can be inserted in a guiding catheter GC together with the microcatheter MC, and taken (retrieved) out of the body as a result of being moved through the guiding catheter GC.

This method is suitable for use in patients 8 hours or more after blood clot formation. This is because, in such cases, blood clots are often harder and tend to easily come off.

The stent system 1 according to the embodiment has advantageous effects, for example, as described below.

(1) The stent system 1 according to the embodiment includes the wire 2; the first stent 3 connected to a distal portion of the wire 2; the first coil 5 that covers and is fixed to a portion of the wire 2 proximal to the first stent 3; and the second stent 4 disposed on a portion of the wire 2 proximal to the first stent 3. The second stent 4 is configured to be movable toward or away from the first stent 3. Therefore, the second stent 4 can be moved to approach the first stent 3 when the first stent 3 has engaged with the blood clot BC. This allows the second stent 4 to hold or cover the first stent 3 when the first stent 3 has engaged with the blood clot BC. This makes it possible to more reliably capture the blood clot BC in the brain region and to prevent the blood clot BC from coming off, even when during the course of withdrawing the stent system 1, the blood clot BC passes through a blood vessel discontinuously increasing in diameter due to confluence of the blood vessels. The first and second stents 3 and 4 can be aligned on a single axis so that the diameter of the whole of the stent system 1 can remain relatively small.

(2) The second stent 4 has an expandable and contractible opening 41 on a side facing the first stent 3. This allows the second stent 4 to more reliably hold or cover the first stent 3 when the first stent 3 has engaged with the blood clot BC. It should be noted that the opening 41 is not essential. When the opening 41 is not provided, the second stent 4 may have a distal end portion (not opened) configured to push the first stent 3 when the first stent 3 has engaged with the blood clot BC.

(3) The second stent 4 is configured to be movable toward the first stent 3 so as to be disposed at a position facing at least a proximal portion of the first stent 3. This allows the second stent 4 to more reliably hold or cover the first stent 3 when the first stent 3 has engaged with the blood clot BC.

(4) The stent system 1 further includes the second coil 6 that covers and is fixed to a portion of the wire 2 proximal to the second stent 4. The first coil 5 limits the range in which the second stent 4 is movable toward the distal side D1, and the second coil 6 limits the range in which the second stent 4 is movable toward the proximal side D2. This makes it easy to stabilize the behavior of the second stent 4.

(5) The second stent 4 is configured to be closable so as to abut against both the proximal end 52 of the first coil 5 and the distal end 61 of the second coil 6. Thus, the second stent 4 functions as a member to fill the space between the proximal end 52 of the first coil 5 and the distal end 61 of the second coil 6. This provides improved rigidity or strength to the whole of the stent system 1 when the stent system 1 is placed in the microcatheter MC and pushed toward the distal side D1. In particular, this provides increased buckling strength to the stent system 1.

(6) The stent system 1 according to another embodiment is configured such that, when delivered to the brain region, the stent system 1 is movable toward the proximal side while holding the blood clot BC between the first and second stents 3 and 4 after the first stent 3 engages with the blood clot BC. This makes it relatively easy to capture the blood clot BC when the blood clot BC is found in the brain region and thus would otherwise be difficult to retrieve, and makes it possible to take (retrieve) the blood clot BC out of the body. If this method of use is adopted, the feature "the first outer sheath (first coil 5) that covers and is fixed to a portion of the wire 2 proximal to the first stent 3" according to the above embodiment is not essential, and the second stent 4 may or may not be configured to be movable toward or away from the first stent 3.

The feature (6) will be described in more detail. The route through which a blood clot will be retrieved from the brain region inevitably includes blood vessel confluence portions, which discontinuously increase in diameter, and bent portions, which have relatively small radii of curvature, in which the captured blood clot has a high risk of coming off. To address this problem, the stent system 1 according to the present invention is configured such that it can first catch a blood clot between the first and second stents 3 and 4 in the brain region and then can be moved toward the proximal side, so that the blood clot can be prevented from coming off at portions which discontinuously increase in diameter or bent portions which have relatively small radii of curvature. It should be noted that, if the stent system is configured such that it can be first moved toward the proximal side and then capture a blood clot, the captured blood clot can come off at the portions mentioned above.

(7) The stent system 1 is suitable for use in a patient 8 hours or more after blood clot formation. Even when the blood clot BC becomes hard after a long time, the stent system 1 helps capture the blood clot BC relatively easily and take it out of the body while preventing it from coming off. It will be understood that the stent system 1 is also suitable for use in a patient less than 8 hours after blood clot formation.

(8) The first stent 3 is preferably configured to expand while at least a portion of the first stent 3 is located distal to the blood clot BC. In this position, the first stent 3 can easily expand and thus can easily engage with the blood clot BC. It will be understood that the first stent 3 may expand in any other position.

The feature (8) will be described in more detail. Conventionally, the stent is designed to expand so as to press a blood clot against the blood vessel wall by its high expansion force so that the blood clot is grasped radially inwardly and the resulting downsized blood clot is held inside the stent. The stent designed based on this idea expands to break a blood clot in the same position as the blood clot during use. When the stent designed based on this idea is used, it is also difficult to avoid blood vessel damage caused by the high expansion force of the stent. In contrast, according to an embodiment of the present invention, the stent system 1 is designed based on such an idea that a blood clot should not be broken or downsized but should be held between the first and second stents 3 and 4, although such an idea is non-limiting. Based on such an idea, the first stent 3 does not need to exert a high expansion force. Based on such an idea, the first stent 3 is designed to expand when at least a portion of the first stent 3 is located distal to the blood clot BC, so that at least part of the blood clot BC is placed between the first and second stents 3 and 4. In addition, even when the expansion force of the first stent 3 is low, the blood clot can be easily retrieved. In the case of such a technical idea, the stent preferably should not radially penetrate the blood clot. According to an embodiment of the present invention, the stent does not need to exert a high expansion force to break a blood clot, which can minimize the damage to blood vessels.

While preferred embodiments of the present invention have been described, it will be understood that the embodiments described above are not intended to limit the present invention and the present invention may be implemented in various ways.

EXPLANATION OF REFERENCE NUMERALS

1: Stent system
2: Wire
3: First stent
4: Second stent
5: First coil (first outer sheath)
6: Second coil (second outer sheath)
41: Opening
44: Marker member
52: Proximal end
61: Distal end
BC: Blood clot
BV: Blood vessel
D1: Distal side
D2: Proximal side
MC: Microcatheter
R: Coil-free region

What is claimed is:

1. A stent system for use in retrieving a blood clot from a brain region, the stent system comprising:
    a wire;
    a first stent connected to a distal portion of the wire;
    a first outer sheath that covers and is fixed to a portion of the wire proximal to the first stent;
    a second stent disposed on a portion of the wire proximal to the first stent; and
    a second outer sheath that covers and is fixed to a portion of the wire proximal to the second stent,
    wherein the second stent is configured to be movable toward or away from the first stent, and
    wherein the second stent abuts simultaneously against both a proximal end of the first outer sheath and a distal end of the second outer sheath when the second stent is completely closed.

2. The stent system according to claim 1, wherein the second stent has an expandable and contractible opening on a side facing the first stent.

3. The stent system according to claim 2, wherein the second stent is configured to be movable toward the first stent so as to be disposed at a position facing at least a proximal portion of the first stent.

4. The stent system according to claim 1, wherein the first outer sheath limits a range in which the second stent is movable toward a distal side, and the second outer sheath limits a range in which the second stent is movable toward a proximal side.

5. The stent system according to claim 1, wherein the second stent is configured to have an outer diameter substantially equal to outer diameters of the first outer sheath and the second outer sheath.

6. A stent system comprising:
    a wire;
    a first stent connected to a distal portion of the wire;
    a first outer sheath that covers and is fixed to a portion of the wire proximal to the first stent;
    a second stent disposed on a portion of the wire proximal to the first stent; and
    a second outer sheath that covers and is fixed to a portion of the wire proximal to the second stent, wherein the second stent abuts simultaneously against both a proximal end of the first outer sheath and a distal end of the second outer sheath when the second stent is completely closed, and wherein the stent system is configured to be movable toward the proximal side while holding a blood clot between the first stent and the second stent after the first stent engages with the blood clot, when the stent system is delivered to the brain region.

7. The stent system according to claim 6, wherein the stent system is for use in a patient who has passed eight hours or more after blood clot formation.

8. The stent system according to claim 6, wherein the first stent is configured to expand while at least a portion of the first stent is located distal to the blood clot.

9. The stent system according to claim 6, wherein the second stent is configured to have an outer diameter substantially equal to outer diameters of the first outer sheath and the second outer sheath.

\* \* \* \* \*